United States Patent [19]
Eisenberg

[11] Patent Number: 4,838,874
[45] Date of Patent: Jun. 13, 1989

[54] FLUID CONTAINER HAVING A ONE WAY VALVE

[76] Inventor: Melvin I. Eisenberg, 3849 Swanson Ct., Gurnee, Ill. 60031

[21] Appl. No.: 321

[22] Filed: Jan. 5, 1987

[51] Int. Cl.⁴ .............................................. A61M 3/00
[52] U.S. Cl. .................................. 604/262; 604/408; 383/44
[58] Field of Search ............... 604/262, 322, 323, 403, 604/408, 409; 251/342; 137/847; 383/35, 43, 44, 49, 50, 57

[56] References Cited
U.S. PATENT DOCUMENTS

| | | | |
|---|---|---|---|
| 356,544 | 1/1887 | Parker | 604/262 |
| 3,102,676 | 9/1963 | Danelli et al. | 383/44 |
| 3,282,412 | 11/1966 | Corella et al. | 383/44 |
| 3,307,549 | 3/1967 | Zackheim | 383/44 |
| 3,473,532 | 10/1969 | Eisenberg | 604/262 |
| 3,724,461 | 4/1973 | Eisenberg | 604/262 |
| 3,734,154 | 5/1973 | Polk | 383/35 |

Primary Examiner—Stephen C. Pellegrino
Assistant Examiner—Ralph Lewis
Attorney, Agent, or Firm—Jerome Goldberg

[57] ABSTRACT

A container for fluid including a front flexible wall and a rear flexible wall sealed together along marginal portions thereof to define a body for holding fluid and unsecured along other portions thereof to provide a fluid supply opening. A valve is positioned in said supply opening between the front and rear walls, to provide a fluid inlet passageway when the valve is in an open condition and to close the fluid inlet passageway when the valve is in a closed condition. The valve comprises a flexible inner sheet and a resilient or spring sheet opposed to each other. The inner sheet is normally in contact with the spring sheet for closing the inlet passageway. The inner sheet and spring sheet extending outward from each other upon the application of an external force for opening the fluid inlet passageway, so that fluid may pass between the inner sheet and the spring sheet and into the body of the container. Pockets are provided inside the container adjacent the valve for tightening the contact of the inner sheet and spring sheet during the valve closed condition, in the event fluid flows back toward the valve. Fluid inserted into the container pulls the rear wall more taut to tug against the spring sheet. This causes the spring sheet in response to arc and thereby form a convex surface or maintain a convex arc, for forcing the inner sheet into a tight and sealing concave contact with the convex surface of the spring sheet.

8 Claims, 3 Drawing Sheets

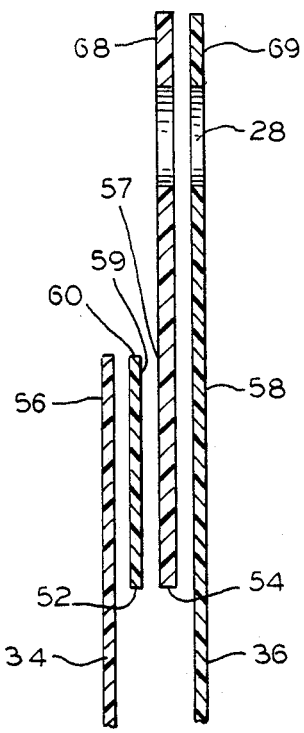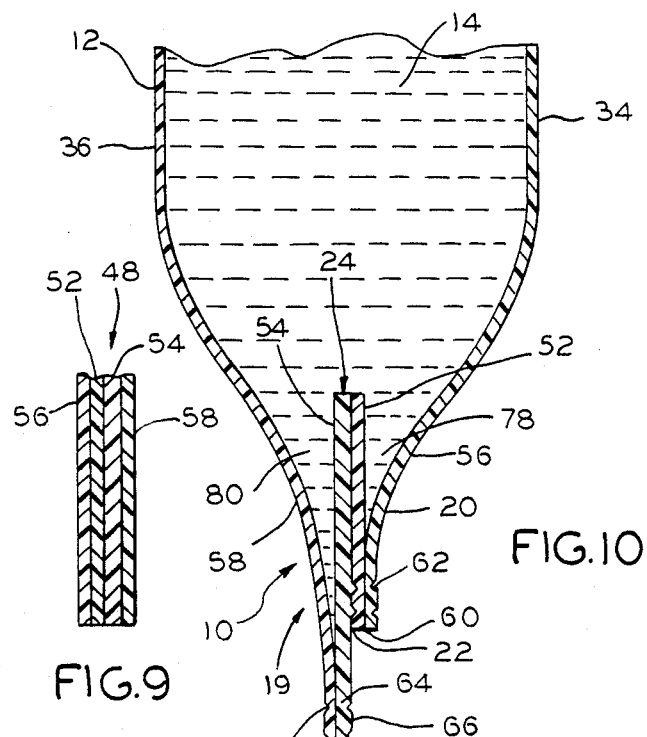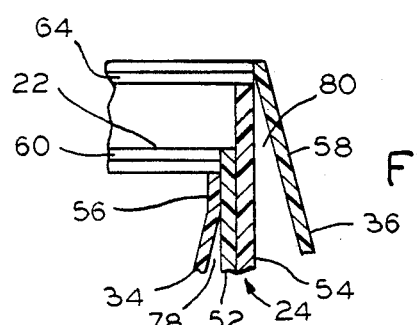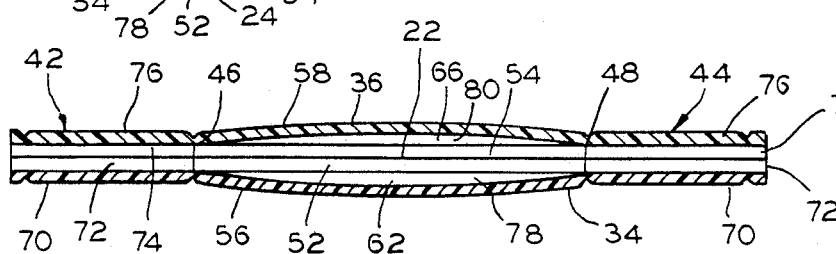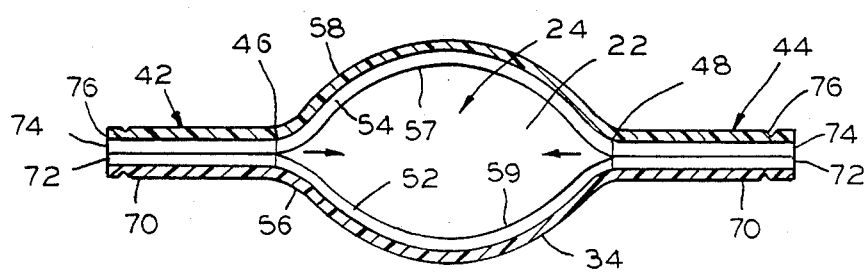

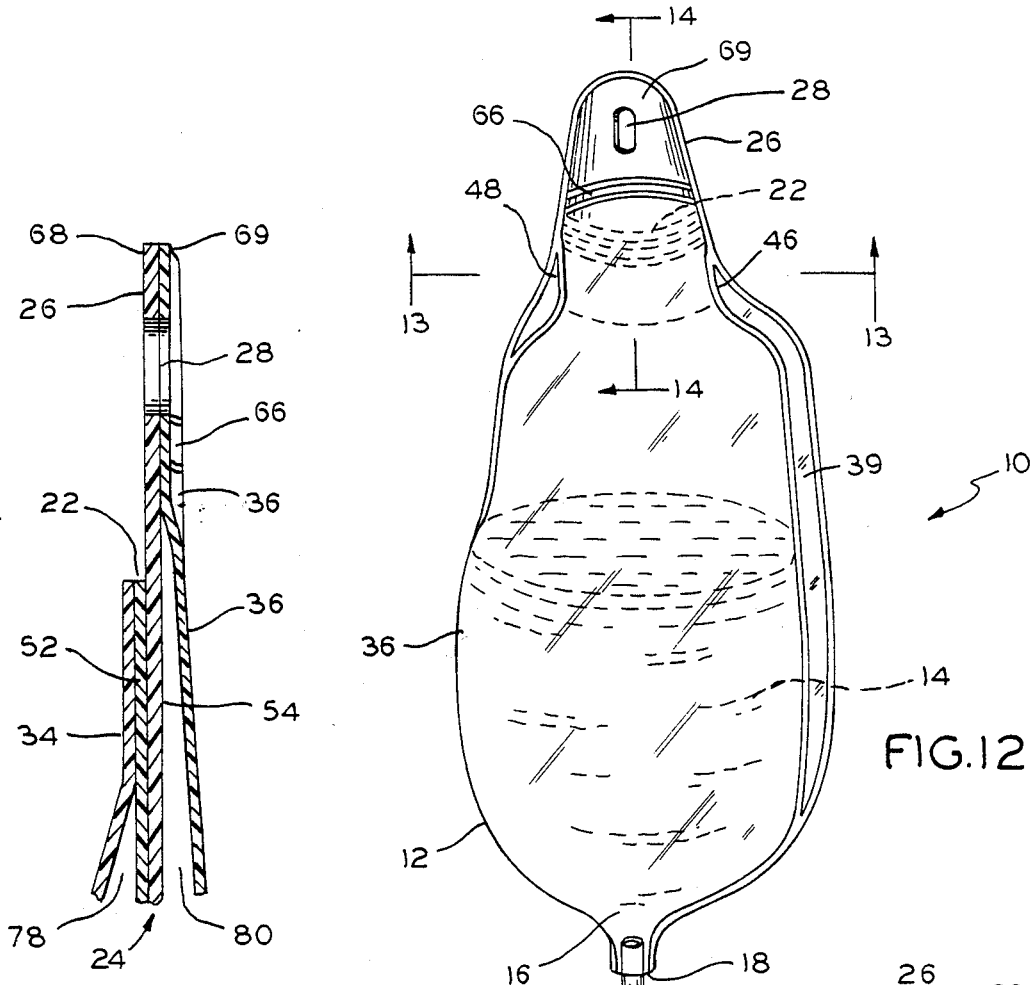
FIG.12
FIG.14
FIG.15
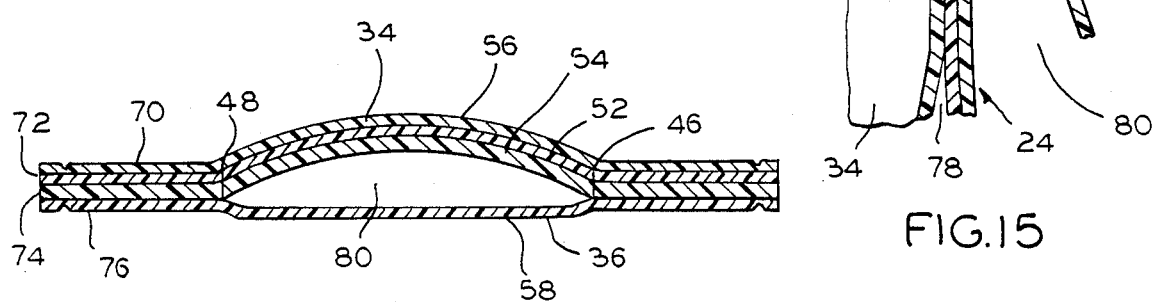
FIG.13

FLUID CONTAINER HAVING A ONE WAY VALVE

BACKGROUND OF THE INVENTION

This invention relates generally to containers for fluids having a one way valve, and more specifically relates to a disposable fluid container having a one way valve and suitable for use as an enema and douche bag and the like.

The disposable fluid containers for use, for example, as enema or douche bags or otherwise are commonly found in hospitals, nursing homes and other health care facilities. Generally, these type bags comprise a pair of confronting sheets of flexible plastic material, such as polyvinyl chloride, heat sealed together along marginal areas thereof except at locations to provide a fluid supply opening and an outlet opening.

My U.S. Pat. No. 3,473,532, granted Oct. 21, 1969, and entitled "FLUID CONTAINER BAG WITH SELF CLOSING ONE-WAY VALVE," discloses a prior used disposable container formed from a pair of confronting flexible walls secured together along marginal portions and unsecured along other portions thereof to form a fluid supply opening. A one-way valve is mounted in the supply opening and comprises a pair of flat, flexible confronting valve walls connected together along side margins and unconnected at the upper and lower ends. A sheet of resilient material permanently arched, pulls the valve walls over its convex side for closing the valve. The application of a squeezing force straightens the resilient sheet to open the valve for flowing fluid between the valve walls.

Another disposable container previously used is disclosed in my U.S. Pat. No. 3,724,461, granted Apr. 3, 1973, and entitled "CONTAINER WITH SELF-CLOSING ONE-WAY VALVE." The container described therein includes a pair of confronting walls unsecured along a portion thereof to form a supply opening. A one-way valve is mounted in the supply opening and comprises a pair of confronting flat walls of flexible material, secured together along side margins thereof to form a sleeve like structure open at the opposite ends thereof, and further secured to the container walls. An arcuate spring member is secured to and extends across the outside of one of the valve walls and the convex side of the spring member forces the valve walls together. Spaced above the arcuate spring member and located between the valve walls are two curving spring members having concave faces confronting each other. The squeezing of the confronting spring members expands the same further outward from each other, and the valve walls in response are caused to balloon outwardly, forming a large fluid inlet passageway between the confronting spring members and between the valve walls.

The aforedescribed disposable containers having one way valves afforded a tight and secure seal against any fluid leakage, and are specifically suitable in those instances where the fluid containers are subject to extremely rough handling. However, such tight sealed disposable containers are not necessary or needed for every health care application requiring a one way fluid container.

Due to the wide and extensive use of the disposable container, and the continued upward spiraling of medical costs, there is an urgent need in the market place for a lower cost disposable container having a one way valve but still providing the desired function. The subject invention by simplifying the valve structure, has provided a low cost and functional disposable fluid container with a one way valve.

SUMMARY OF THE INVENTION

The fluid container of this invention comprises a front flexible wall confronting a rear flexible wall sealed along marginal portions and unsecured along portions thereof for providing a fluid supply opening. A valve is secured in the fluid supply opening between the front and rear walls and includes a flexible sheet and a spring sheet attached to each other along side margins thereof in a sleeve like configuration, open at the top and bottom thereof, to provide a fluid inlet passageway between the inner sheet and the spring sheet. The inner sheet is normally in contact with the spring sheet for closing the fluid inlet. Upon the application of a squeezing force, the spring sheet and the inner sheet arc or bow outward away from each other to provide opposed concave faces, thereby opening the fluid inlet. The fluid inlet is closed upon releasing the squeezing force. The spring sheet may be a bendable, rigid and resilient material, such as a suitable plastic.

Pockets are formed respectively between one of the walls and the inner sheet and the other wall and the spring sheet to more securely tighten the contact between the inner sheet and the spring sheet in the event fluid flows back toward the fluid inlet passageway when the valve is closed.

The rear wall is attached to the spring sheet so that fluid inserted downward into the container pulls the rear wall more taut, causing or maintaining arcing of the spring sheet, so that the front side of the spring sheet is a convex configuration. This forces the inner sheet into a concave and tight contact with the convex surface of the spring sheet for more securely sealing the fluid inlet passageway when the valve is closed.

Moreover, the curving of the spring sheet so that the front surface thereof is convex for contacting a concave surface of the inner sheet provides a tight closure of the fluid inlet passageway. The cooperation of the rear wall of the container and the spring sheet maintains said convex configuration when the fluid in the container causes the rear wall to be taut.

It is therefore a primary object of the invention to provide a simplified one way valve for a disposable fluid container.

Another object is to provide a disposable container having a one way valve which is a suitable replacement or alternative for many of the disposable containers having complex and costly constructed fluid valves.

Still another object is to utilize the fluid that may flow back toward the fluid inlet passageway when the fluid inlet is closed, for providing a still tighter closure to prevent outflow through the closed fluid inlet passageway.

It is a primary feature of the invention to provide a valve means for a container comprising an inner sheet and a spring sheet normally in contact with each other for closing the fluid inlet passageway into the container and spreading apart upon the application of an external force for opening the fluid inlet passageway, to permit fluid to be inserted into the container by flowing between the inner sheet and the spring sheet.

Another feature is to provide a fluid container having an inner pocket adjacent the inner sheet and another inner pocket adjacent the spring sheet for receiving any back flow of fluid to tighten the contact of the inner sheet with the spring sheet when the fluid inlet is closed.

Still another feature is to attach the rear wall of the container to the spring sheet so that the force of the fluid in the container will cause the rear wall to pull on the spring sheet and provide a convex surface configuration for the spring sheet tightly contacting a concave configuration for the inner sheet.

BRIEF DESCRIPTION OF THE DRAWINGS

Referring to the drawings in which the same characters of reference are employed to indicate corresponding similar parts throughout the several figures of the drawings:

FIG. 6 is a cross sectional view, taken on the plane of the line 6—6 in FIG. 1, viewed upward in the direction indicated, and showing the valve means in a closed condition;

FIG. 7 is a similar cross sectional view as FIG. 6, but showing the valve means in an open condition;

FIG. 8 is a fragmentary sectional view of the several sheets of material used in the construction of the container;

FIG. 9 is a sectional view, taken on the plane of the line 9—9 in FIG. 1, viewed in the direction indicated, and showing the various parts connected at the joints;

FIG. 10 is a fragmentary inverted sectional view to show the valve in a closed condition and the fluid having flowed into the front and rear pockets;

FIG. 11 is a fragmentary sectional perspective view to show the front pocket and rear pocket when the valve means and the fluid inlet are in a closed condition;

FIG. 12 is a perspective view of the rear side of the container having fluid stored therein;

FIG. 13 is a cross-sectional view, taken on the plane of the line 13—13 in FIG. 12, viewed in the direction indicated, and showing the container closed and illustrating the convex surface of the spring sheet in contact with the concave surface of the inner sheet;

FIG. 14 is a cross-sectional view, taken on the plane of the line 14—14 in FIG. 12, and viewed in the direction indicated; and FIG. 15 is a fragmentary sectional perspective view to show the convex front surface of the spring sheet.

DESCRIPTION OF THE PREFERRED EMBODIMENT

Figure 1:
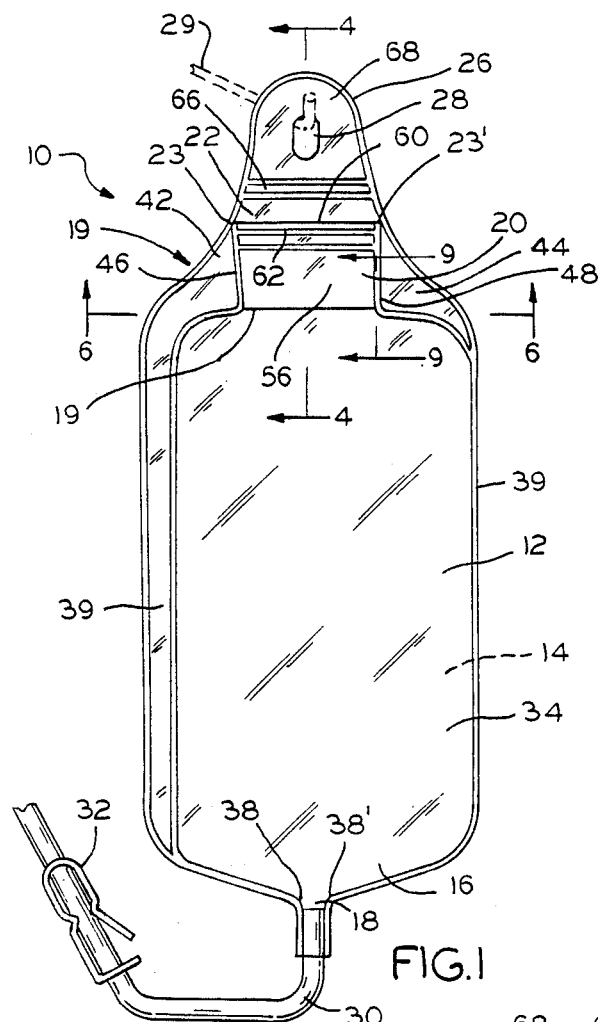
FIG. 1 is a front elevational view of the fluid container, embodying the principles of the invention, and showing the container positioned on a rod.
Figure 2:
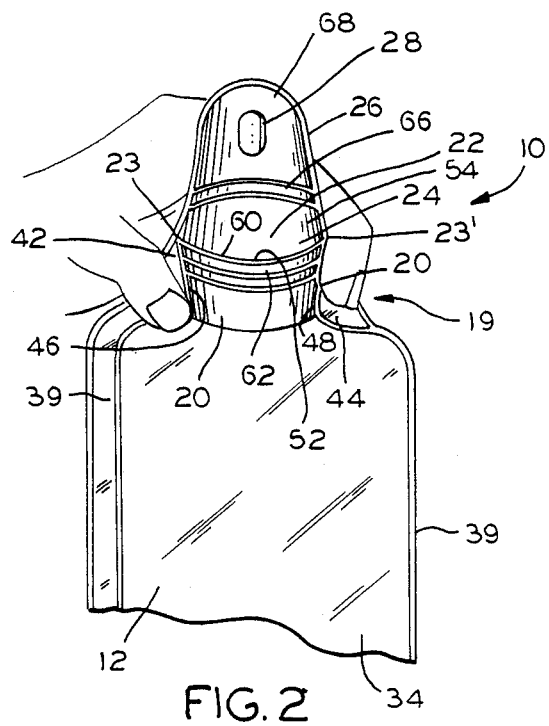
FIG. 2 is a fragmentary perspective view of the fluid container showing the container open and ready for filling with fluid.
Figures 3, 4, 5:
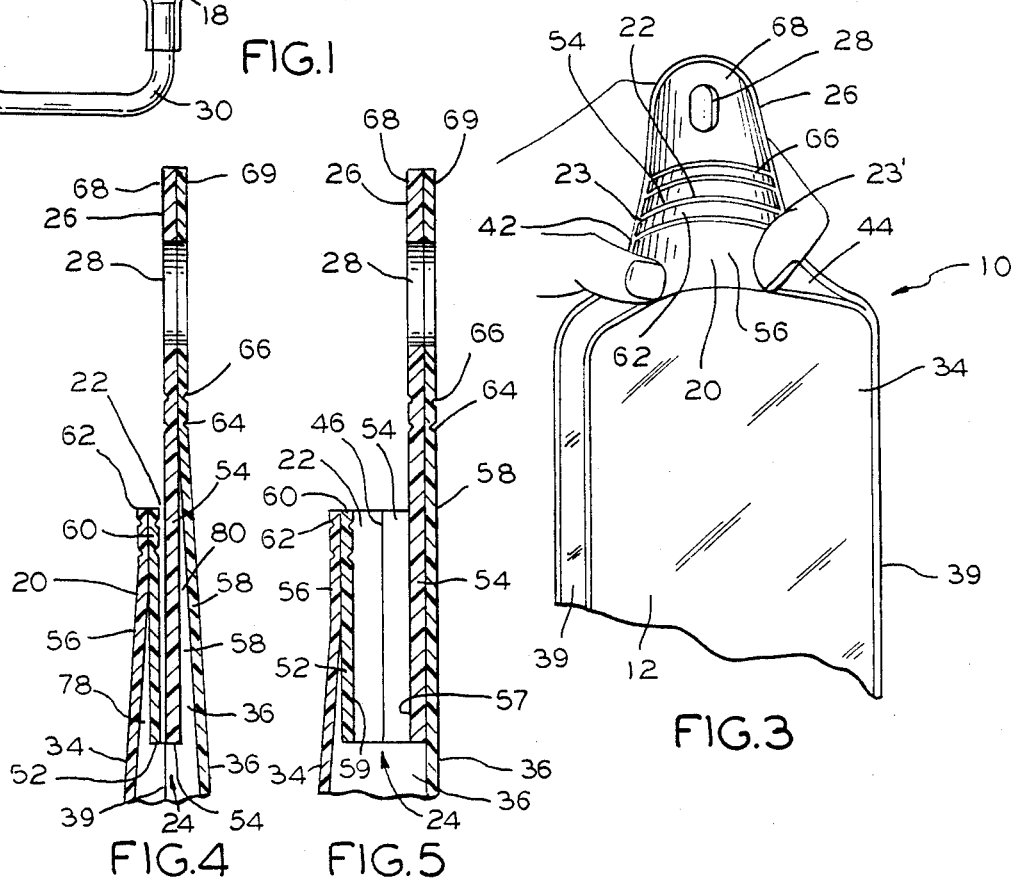
FIG. 3 is a fragmentary perspective view of the fluid container showing the container in a closed condition.
FIG. 4 is a fragmentary sectional view taken on the plane of the line 4—4 in FIG. 1, and showing the valve means and the fluid inlet passageway in a closed condition.
FIG. 5 is a fragmentary sectional view similar to FIG. 4, but showing the valve means and fluid inlet passageway in an open condition.

Referring now more particularly to FIG. 1 of the drawings, the reference numeral 10 indicates generally a fluid container having many uses and applications but is specifically suitable for use as an enema or douche bag. The fluid container 10 comprises a body portion 12, wherein the fluid 14 is stored, a bottom end 16 having a fluid outlet opening 18, and a fluid supply input means 19 including a neck portion 20 having a fluid inlet 22 between points 23, 23' (FIGS. 1 and 2) and a one way valve means indicated generally by the reference numeral 24. When the valve 24 is open the inlet 22 is open (FIG. 2), and when the valve 24 is closed the inlet 22 is closed (FIGS. 4 and 10).

A handle 26 extends upward from the neck portion 20 for holding or carrying the container 10. An oblong opening 28 is formed in the handle 26, sized to receive a finger for gripping when carrying or lifting the container 10, and also to be used for hanging the container 10 on a rod 29 in a vertical position as shown in FIG. 1.

A feed tube 30 extends inside the outlet opening 18 and is in communication with the interior of the container 10. A clamp means 32 controls the flow of liquid 14 out from the container 10 and through the feed tube 30.

The container 10 comprises a front flexible wall 34 (FIG. 1) opposed and confronting a rear flexible wall 36 (FIGS. 8 and 10). Preferably, the walls 34,36 are made from a heat sealable synthetic plastic material, such as flexible polyvinyl chloride material.

The walls 34,36 are heat sealed together along marginal portions 39 thereof, except between points 38,38' which define the outlet opening 18 and between points 23,23' where the fluid inlet 22 and valve means 24 are located. The feed tube 30 is sealed to the walls 34,36 between the points 38,38'.

Shoulders 42,44 extend outward from the neck 20 and are bendable frontward and backward respectively along joints 46,48. When the neck 20 is squeezed between the joints 46,48, the valve means 24 opens, thereby opening the fluid inlet 22, as may be seen in FIG. 2. When the squeezing force is removed the valve means 24 returns to a closed position, thereby closing the fluid inlet 22 (FIG. 3).

The valve means 24 (FIG. 4) includes a flexible inner sheet 52 and a spring sheet 54 interposed between the front side 56 and the rear side 58 of the neck portion 20. The front face 57 of the spring sheet 54 is opposed to the rear face 59 of the inner sheet 52. The front side 56 is an integral part of the front wall 34 and the rear side 58 is an integral part of the rear wall 36. The inner sheet 52 may be formed from a material similar to that of the walls 34,36, such as a flexible polyvinyl chloride material, and the spring sheet 54 may be a sheet of rigid and resilient polyvinyl chloride material.

The joints 46,48 are heat sealed lines which define the opposite vertical or side edges of the neck portion 20, as viewed in FIG. 1. The joint 46 seals together the vertical or side edges of the front side 56, the inner sheet 52, the spring sheet 54 and the rear side 58. The joint 48 (FIG. 9) seals together the opposite vertical or side edges of the front side 56, the inner sheet 52, the spring sheet 54, and the rear side 58.

The top or outer end 60 of the inner sheet 52 is heat sealed to the top of the front side 56 of the neck 20 to form a lateral rim 62 (FIGS. 1 and 4). The top or outer end 64 of the spring sheet is heat sealed to the rear side 58 of the neck 20 along a seam line 66, located above the rim 62.

The fluid inlet 22 is between the inner sheet 52 and the spring sheet 54. The inlet 22 is open when the inner sheet 52 and the spring sheet 54 are forced outward away from each other.

The handle 26 includes a forward face 68 which may be a flexible rigid polyvinyl chloride material and a back side 69 which may be a flexible polyvinyl chloride material. The handle 26 extends upward from the seam 66.

The shoulders 42,44 are each constructed from four substantially triangular segments including a flexible front segment 70, a flexible inner segment 72, a rigid inner segment 74 and a rear segment 76. Turning now specifically to FIGS. 1, 6 and 7, it will be seen that the front segment 70 is formed from the same sheet of material that forms the front side 56 (front wall 34), the inner segment 72 is formed from the same sheet of material that forms the flexible inner sheet 52, the rigid segment 74 is formed from the same sheet of material that forms the spring sheet 54, and the rear segment 76 is formed from the same sheet of material that forms the rear side 58 (rear wall 36).

Moreover, as may be seen from FIGS. 4, 6 and 8, the front face 68 of handle 26 and the rigid segments 74 of the shoulders 42,44 are formed from the same rigid sheet of material that forms the spring member 54 of the valve means 24. Also, the rear wall 36 covers the entire back of the fluid container 10 (FIG. 8).

Turning now to FIGS. 4, 6, 10 and 11, it will be seen that a front inside pocket 78 is formed inside the container 10 between the front side 56 of neck 20 and the inner sheet 52 and bounded by the joints 46, 48 and the rim 62. A rear inside pocket 80 is formed inside the container 10 between the spring sheet 54 and the rear side 58 of the neck 20 and bounded by the joints 46,48 and the seam line 66.

The pockets 78,80 are enlarged when the fluid 14 inserted into the container 10 force the front wall 34 and the rear wall 36 to spread further apart from each other. This causes the front side 56 to move outward from the inner sheet 52 to expand the front pocket 78, and the rear side 58 to move further outward from the spring sheet 54 to expand the rear pocket 80.

When fluid flows into pockets 78,80, an inward force is applied against the inner sheet 52, and an opposite force is applied against spring sheet 54 to cause tighter contact of the inner sheet 52 with the spring sheet 54. Thus, the effect of having fluid in the pockets 78,80 is to more tightly and securely close the valve 24 and fluid inlet 22.

The fluid 14 flows into the pockets 78,80, for example, when filling the container 10 or in the event the container 10 is inverted or laid on its side or from a jarring action. The fluid 14 only flows one way into the valve 24 and the fluid inlet 22, and cannot flow out from the valve 24 and inlet opening 22 when closed, due in part to the locking action of the fluid in the pockets 78,80.

Prior to opening the valve 24 and the fluid inlet 22 for inserting fluid into the container, the spring sheet 54 is substantially flat and in contact with the inner sheet 52. The inner sheet is also flat and tightly pulled across the spring sheet 54. The shoulders 42,44 are in substantial alignment with the neck 20 (FIG. 1). To open the valve 24 and the fluid inlet 22, the shoulders 42,44 are pivoted at the joints 46,48, preferably to the rear, to expose the joints 46,48 for gripping. The neck is then gripped by the thumb contacting one of the joints 46,48 and another finger of the same hand contacting the other joint 46,48, and the neck 20 is then squeezed therebetween. This causes the spring sheet 54 to arc or bow outward, and in response the inner sheet 52 also bows outward and moves away from the spring sheet 54. As may be seen in FIG. 7, when the valve means 24 is open the front face 57 of the spring sheet 54 is concave and opposed to the concave front face 59 of the inner sheet 52. Also, due to the squeezing force the joints 46,48 are closer to each other than when the valve means 24 and fluid inlet 22 are closed. Now, the valve means 24 and fluid inlet 22 are open and the container 10 may be filled with fluid by flowing the fluid between the inner sheet 52 and spring 54.

To close the valve 24 and the fluid inlet 22 after fluid is inserted therein, the squeezing force applied between the joints 46,48 is removed and the spring sheet 54, due to its resilient force, moves inward and straightens toward its normal flat condition. As the spring sheet 54 moves inward, it causes the joints 46,48 to move away from each other, thereby pulling the inner sheet 52 toward and in tensioned contact with the spring sheet 54. Now the valve 24 and fluid inlet 22 are closed (FIG. 3).

To more securely close the valve 24 and fluid inlet 22 (FIG. 3), a slight squeezing force is applied to the neck 20 after the shoulders are pivoted to the rear, to cause the spring sheet 54 to arc slightly, so that its front face 57 is convex, and responsively the inner sheet 52 also arcs so that its opposed rear face 59 is concave. The concave rear face 59 of the inner sheet 52 stretches over the convex face 57 of the spring sheet 54. This smooths out the inner sheet 52 and provides more clinging and greater adherence of the inner sheet 52 to the spring sheet 54. Also, the fluid 14 in the container 12 provides a force pulling the outside wall 36 away from the spring sheet 54, and maintains the convex configuration for the spring sheet thereby providing tight closure of the fluid inlet 22.

If the force of the fluid in the container is not sufficient to maintain the convex configuration for the front side 56 of the spring sheet 54, the spring sheet 54 due to its resilient force, may tend to return to its normal substantially flat position, and the inner sheet in response will also straighten while still maintaining closure contact with the spring sheet 54.

If the flexible wall 34 or 36 of the container or the inner sheet 52 have creased or wrinkled, it is desirable to rub the front side 56 and rear side 58 against the rigid spring sheet 54 and the inner sheet 52. This will smooth out such creases and wrinkles, so that the inner sheet 52 and the spring sheet 54 cling and adhere more firmly to each other to provide sealed closing of the fluid inlet 22.

Thus, the valve 24 includes the inner sheet 52 and the spring sheet 54 positioned in the neck 20 of the container 12 and sealed together along their side margins and also sealed at the side margins to the front and rear walls 34,36. The top 60 of the inner sheet 52 is sealed to the front wall 34 and the top 64 of the spring sheet 54 is sealed to the rear wall 36. Hence, the attached inner sheet 52 and spring sheet 54 have a sleeve like configuration whereby the valve 24 is closed when the inner sheet 52 and the spring sheet 54 are in contact with each other; and the valve 24 is open when the inner sheet 52 and the spring sheet 54 spread apart forming confronting concave faces with the open fluid inlet passageway 22 therebetween.

The normal position for the spring sheet may be bowed to provide a convex surface in the front face 57 in contact with a concave front face 59 for the inner sheet 52, to afford tighter contact between the surfaces when the valve 24 is closed. The bow in the spring sheet 54 causes the flexible inner sheet 52 to also bow into taut contact with the spring sheet 54.

Various modifications of the invention of a fluid container having a one way valve described herein are within the spirit and scope of the invention, the scope of which is limited soley and defined by the appended claims.

I claim:

1. A container for fluid comprising:
    a front flexible wall and a rear flexible wall secured together along certain edge portions thereof to define a body for holding said fluid, and unsecured along outer portions thereof to provide a fluid supply opening;
    a valve means positioned in said supply opening and having a closed condition and an open condition, said valve means including:
    a flexible inner sheet;
    a spring sheet constructed from a flexible, rigid and resilient material, said inner sheet and said spring sheet being opposed to each other and attached to each other along opposite side margins thereof and unattached to each other at the upper and lower ends to form an open ended sleeve like configuration and provide a fluid inlet passageway between the inner sheet and spring sheet, each of said margins being attached to the front and rear walls, said spring sheet extending above said inlet passageway and formed to provide a handle for said container, said upper end of the inner sheet being attached to said front wall and the said rear wall being attached to said handle;
    a first pocket formed between said one of the walls and said inner sheet; and
    a second pocket formed between said other wall and said spring sheet, said pockets receiving fluid flowing back from the body of the container toward said valve means to more securely maintain the spring sheet in contact with the inner sheet, said inner sheet and said spring sheet being in contact with each other to provide said valve closed condition for closing said fluid inlet, said spring sheet and said inner sheet responding to the application of an external force and extending outward from each other to provide said open valve condition for opening said fluid inlet, said spring sheet and said inner sheet returning toward each other upon removal of said external force.

2. The container of claim 1 includes:
    an upper end having a pair of spaced apart shoulders, said fluid supply opening being between said shoulders; and
    the attachment of said side margins to the front and rear walls forming opposed pivotal joints, to permit the shoulders to be pivoted frontward and backward, for applying a squeezing force between the joints for opening said fluid inlet passageway as the inner sheet and spring sheet extend outward from each other.

3. The container of claim 2, wherein:
    one of said shoulders is positioned between one of said joints and the outer edges of the attached front and rear walls and the other said shoulder is positioned between the other said joint and the opposite outer edges of the attached front and rear walls, each of said shoulders including portions of the inner sheet and the spring sheet between the front and rear walls, said portions of the inner sheet and spring sheet not being in communication with the inlet passageway.

4. The container of claim 1, wherein said valve means is in a closed condition for closing said fluid inlet passageway when said spring sheet has a convex configuration in contact with a concave configuration of said inner sheet.

5. The container of claim 1, wherein:
    the upper end of the inner sheet is attached to the front wall and the upper end of the spring sheet is attached to the rear wall, the front side of the spring sheet having a convex configuration in contact with a concave configuration of said inner sheet when the valve is in said closed condition for closing said fluid inlet passageway, the cooperation of said rear wall with said spring sheet maintaining said spring sheet in a convex configuration in contact with the concave configuration of the inner sheet when the force of fluid in said container pulls the rear wall away from said spring sheet.

6. The container of claim 1, wherein said valve means is in a closed condition for closing said fluid inlet passageway when said spring sheet and said inner sheet are substantially flat and in contact with each other.

7. The container of claim 1, wherein:
    the cooperation of said rear wall with the handle and spring sheet when fluid is stored in said container, causing said spring sheet to arc and provide a convex surface in contact with a concave surface of said inner sheet when the valve is in a closed condition.

8. The container of claim 1 wherein:
    said rear wall is attached to said handle above said inlet passageway.

* * * * *